United States Patent
Gautschi

(12) 
(10) Patent No.: US 6,387,431 B1
(45) Date of Patent: May 14, 2002

(54) DICARBOALKOXY DIOXOLANES AS FLAVORING AGENT RELEASING COMPOUNDS

(75) Inventor: Markus Gautschi, Zeiningen (CH)

(73) Assignee: Givaudan SA (CH)

( * ) Notice: Subject to any disclaimer, the term of this patent is extended or adjusted under 35 U.S.C. 154(b) by 0 days.

(21) Appl. No.: 09/508,944

(22) PCT Filed: Jul. 7, 1999

(86) PCT No.: PCT/CH99/00304

§ 371 Date: Jul. 19, 2000

§ 102(e) Date: Jul. 19, 2000

(87) PCT Pub. No.: WO00/04009

PCT Pub. Date: Jan. 27, 2000

(51) Int. Cl.$^7$ ............................................... A23L 1/22
(52) U.S. Cl. ...................... 426/534; 426/573; 426/650; 549/435

(58) Field of Search ................................ 426/534, 536, 426/538, 650, 651, 573, 578; 549/435, 448, 450, 454

(56) References Cited

U.S. PATENT DOCUMENTS 5,144,048 A * 9/1992 Christenson et al. ....... 549/435

OTHER PUBLICATIONS

Sharma et al., Stabilization of Aldehydes as Propylene Glycol Acetals, J. Agric. Food Chem., vol. 46, No. 2, 1998, pp. 654–656.*

* cited by examiner

*Primary Examiner*—Leslie Wong

(57) ABSTRACT

The dicarboalkoxy dioxolanes of formula (I) are stable in acidic aqueous alcoholic and non-alcoholic beverages. Therefore they are useful in food products especially in beverages to stabilize the citral character of these products by releasing citral over a prolonged period.

10 Claims, No Drawings

DICARBOALKOXY DIOXOLANES AS FLAVORING AGENT RELEASING COMPOUNDS

This is a National Stage filing of PCT/CH99/00304 filed Jul. 7, 1999.

The present invention relates to dicarboalkoxy dioxolanes and a citral release preparation containing these compounds.

Aldehydes represent an important class of flavor compounds that are ubiquitous in nature. This class of compounds is also of great value for providing consumer products with additional flavors or odors. However, the high reactivity of aldehydes such as citral can represent a major stability problem in the final product. The chemical properties of aldehydes and their reactivity towards nucleophiles are characterized by the terminal carbonyl group. Aldehydes are easily reduced to the corresponding alcohols, oxidized to carboxylic acids and undergo addition reactions such as also condensation. Due to the conjugated double bond unsaturated aldehydes have a strong tendency to polymerization. Such polymerisation can already take place during a longer storage period. Furthermore, unsaturated aldehydes can also undergo 1,4-addition reactions with sulfur leading to numerous impact flavor compounds (K.-H. Engel, R. Tressl, J. Agric. Food Chem. 1991, 39, 2249).

Citrus oils being a good source for a series of important aldehydes like aliphatic $C_7$–$C_{12}$ aldehydes, citral and citronellal are used in a wide variety of applications. Citral, a mixture of geranial and neral, is one of the key impact components of citrus oils, and can be either isolated from natural raw materials such as lemon grass or can be synthesized e.g. starting from isoprenol. Besides natural citral, which is frequently preferred for its harmony, standardized synthetic citral is generally used in low cost bulk products. Synthetic citral is an important synthetic ingredient for flavors with a total consumption of about 100 tons in 1985 and an annual production of several thousand tons in the US [P. Z. Bedoukian, in Perfumery and Flavouring synthetics, Allured Publishing, Wheaton (1986), pp. 16–18].

Citral plays also a major role in the formulation of alcoholic and non-alcoholic beverages of the citrus type. These citrus beverages have typically a relatively low pH value in the range of 2–4. The stability of citral under these acidic conditions, e.g. aqueous lemon beverages, lemon oil emulsions etc., has been well investigated (H. Friedrich, B. A. Gubler, Lebensm.-Wiss. u. Technol. 1978, 11, 215–218; ibid. 1978, 11, 316–318). It has been shown that citral is degraded via a series of cyclization and oxidation reactions leading to a variety of compounds like p-cymene, p-cresol, carvone and p-methylacetophenone being responsible for the off-flavor in citrus beverages (K. Kimura, H. Nishimura, I. Iwata, J. Mizutani, J. Agric. Food Chem. 1983, 31, 801–804; P. Schieberle, W. Grosch, Z. Lebensm. Unters. Forsch. 1989, 189, 26; E. J. Freeburg, B. S., G. A. Reineccius, J. Scire, Perfumer & Flavorist 1994, 19, July/August, 23–32).

According to a current principal strategy aldehydes are stabilized in consumer products by admixing with a matrix that slows or prevents release of the aldehydes until the product is pyrolized, heated, masticated or wetted. As an alternative, the aldehydes may be covalently bound to auxiliary components to form higher molecular weight molecules of low volatility. The aldehyde is then released upon pyrolysis, heating or solvolysis. Acetals have also been used as vehicles to covalently bind aldehyde flavorants. For example, U.S. Pat. No. 4,296,137 describes the use of 1-ethoxy-1-ethanol acetate as a flavor or fragrance enhancer of a wide variety of consumable materials. U.S. Pat. No. 4,280,011 describes the use of acetals as aldehyde generators in food applications. U.S. Pat. No. 3,625,709 discloses food flavoring and aroma enhancer compositions consisting of acetaldehyde combined with carbohydrates. These compositions release acetaldehyde when combined with hot or cold water. EP-A1-0 501 645 describes the preparation of tartrate acetals or ketals as flavor-releasing additives for smoking compositions which, under smoking conditions, release volatile aldehyde or ketone flavors into the smoke. U.S. Pat. No. 5,144,048 describes dicarboalkoxy dioxolane derivatives as precursors which release an odorant molecule. They are useful in tobacco, cooked food and chewing gum.

Since all these methods for stabilizing labile aldehydes are well known, it seemed obvious to test citral dimethyl acetal and citral propylene glycol acetal as possible citral precursors (A. Sharama, S. Nagarajan, K. N. Gurudutt, J. Agric. Food Chem. 1998, 46, 654–656). However, these compounds are rapidly hydrolized in aqueous solutions and in acidic aqueous alcoholic and non-alcoholic beverages. Due to their short half lives these compounds cannot be considered as useful for a consumer product and the instability of citral in acidic aqueous alcoholic and non-alcoholic beverages remains still unsolved.

This problem is solved by the present invention which provides dicarboalkoxy dioxolane derivatives of formula I:

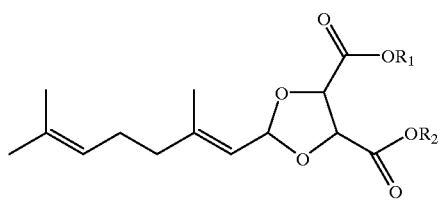

wherein $R_1$ and $R_2$ are the same or different and stand for H, straight or branched alkyl, alkenyl, cycloalkyl, aryl, aralkyl.

It has been surprisingly found that the dicarboalkoxy dioxolanes of formula I, contrary to citral dimethyl acetal and citral propylene glyco acetal (A. Sharama, S. Nagarajan, K. N. Gurudutt, J. Agric. Food Chem. 1998, 46, 654–656), have much longer half lives in acidic aqueous alcoholic and non-alcoholic beverages. In contrast to citral dimethyl acetal and citral propylene glyco acetal the half lives of the dicarboalkoxy dioxolanes of formula I are within a useful range for a consumer product. Surprisingly, the dicarboalkoxy dioxolanes of formula I release citral (geranial and neral) over a prolonged time. It is further surprising that the release rate can be modulated by varying the ester groups $R_1$ and $R_2$. Small groups $R_1$ and $R_2$ give raise to short half lives, whereas bulkier groups and longer alkyl chains give rise to dicarboalkoxy dioxolanes of formula I with long half lives. Hence, using citral release preparations with different release profiles can be designed. This is especially useful for acidic aqueous alcoholic and non-alcoholic beverages with varying shelf lives. E.g. a citral release preparation with a short half life is suitable for an instant beverage, whereas a citral release preparation with a long half life is more suitable for a ready to consume beverage with a certain shelf life.

The compounds of formula I are not limited to any particular stereoisomer and all possible stereoisomers are included within the scope of the invention.

The compounds of formula I are useful in consumer products, such as food products, especially in aqueous, alcoholic and non-alcoholic beverages of the citrus type. They stabilize the citral character of these products by releasing citral over a prolonged period. The release preparations are especially useful for instant beverages prepared by admixing dry beverage powders with water.

The citral release preparation may comprise a single dicarboalkoxy dioxolane derivative of formula I or a mixture of several dicarboalkoxy dioxolane derivatives of formula I. The preparations of the invention may also include (additional) flavors. The dry preparations are stable. After contact with water the flavors are released from preparation immediately, whereas the compounds of general formula I release citral slowly. Due to their long lasting citral taste, the resulting beverages are preferred to beverages without the citral release preparation.

The citral release preparations of the present invention are used in consumer products to provide the characteristic impression of citral over a prolonged period of time. The citral release preparation can be used in combination with citral, they can partially substitute citral usually present in lemon/lime or other flavorings and they can completely replace citral in a flavoring. Preferably the release preparations are used in combination with citral.

The release preparations of the present invention may be powders and may be prepared by methods known to the skilled in the art. The release preparations in form of powders may be prepared by spray drying an emulsion containing one or more derivatives of general formula I. The compounds of general formula I may be added to the emulsion to be dried as such or dissolved in a lipophilic food grade solvent. Preferably plant oils, e.g. vegetable oils, are used. Emulsifying agents and a carrier material having emulsifying properties may be used for the preparation of the emulsions. The carrier materials for the emulsion are selected from materials commonly used for these purposes. Preferably the carrier material is a carbohydrate, a modified starch, a degraded starch (dextrin, maltodextrin), natural resin, an exudate, e.g. gum arabicum, a plant extract, like carragenan, alginates, etc., a protein, e.g. a milk protein or gelatine, combinations of the above or other commonly used carrier materials. As solvent for these emulsions e.g. water or water/ethanol mixtures can be used. Commonly used additives such as artificial sweeteners, food colorants, vitamins, antioxidants, antifoaming agents, taste modifiers, e.g. citric acid, may also be added to the emulsions. Together with the dicarboalkoxy dioxolane derivatives of formula I a flavor composition may be added to the emulsion thus giving a release preparation containing a flavor. The emulsion is then spray dried to obtain a release preparation in powder form generally containing 1% to 30%, preferably from 5% to 20% of the dicarboalkoxy dioxolane derivatives of formula I.

Citral release preparations in form of granules may be prepared as described in WO-A1-9716078. Thereby a fluidized core material is sprayed and granulated with an emulsion containing one or more dicarboalkoxy dioxolanes of formula I. A food or pharmaceutical grade solid material having a diameter of 0.02 to 3.0 mm, preferably from 0.2 to 1.5 mm is used as core material. Preferred core materials are carbohydrates, e.g. a sugar like sucrose, glucose, saccharose or a material having a complex composition, e.g. a fruit power, hydrolized vegetable protein (HVP), inorganic salts, e.g. sodium chloride or citric acid salts. The emulsion to be sprayed contains a carrier material such as carbohydrates, e.g. modified starch, degraded starch (dextrin, maltodextrin), a natural resin, an exudate, e.g. gum arabicum, a plant extract, like carragenan, alginates, etc., a protein, e.g. a milk protein or gelatin, or a combination of these materials. As solvent for these emulsions water or water/ethanol mixtures can be used. The emulsions may also contain commonly used additives such as artificial sweeteners, food colorants, vitamins, antioxidants, antifoaming agents, taste modifiers, e.g. citric acid.

The granules obtained may be additionally coated, e.g. by spraying with a solution or emulsion of a material commonly used for this purpose, e.g. fat, modified cellulose, gelatin, or plant extracts.

Alternatively the dicarboalkoxy dioxolanes of formula I may also be encapsulated alone or together with a flavor composition. Thus, an encapsulated release preparation containing one or more compounds of formula I and a flavor is obtained. The encapsulated release preparations of the invention usually contain 1% to 30% of the dicarboalkoxy dioxolane derivatives of formula I, preferably 5% to 20%.

The amount of citral release preparation used should be sufficient to impart the typical fresh, lemon-like character of citral to the food product and will depend upon the precise organoleptic character desired for the finished product. More of the citral release preparation may be required to provide a full rounded lemon/lime flavor to an unflavored material and less may be required when the intention is to enhance the citral character of an already flavored material.

The dicarboalkoxy dioxolane derivatives of formula I can be readily prepared by methods known to those skilled in the art. (T. W. Greene, P. G. M. Wuts, "Protective Groups in Organic Synthesis" 2nd Ed, John Wiley & Sons, Inc., New York 1991.) The usual method for preparing compounds of this type involves condensation of citral dimethyl acetal with a lower alkyl tartrate in an inert solvent in the presence of an acid catalyst. During the condensation methanol is azeotropically removed. Either catalytic or equimolar amounts of protic or Lewis acids can be used for the condensation. Acids that may be used are p-toluenesulfonic acid, sulfuric acid, phosphoric acid, hydrochloric acid, methanesulfonic acid, pyridinium p-toluenesulfonate, ferric chloride, acidic ion exchange resins, zinc chloride, titanium tetrachloride. Preferred acids include p-toluenesulfonic acid and methanesulfonic acid. Pyridinium p-toluenesulfonate is the most preferred acid.

To remove methanol, a variety of solvents may be used such as toluene, benzene, cyclohexane, xylene, hexane, chlorobenzene, dimethyl formamide and methyl tert-butyl ether. The preferred solvents are cyclohexane and dimethyl formamide. Methyl tert-butyl ether is the most preferred solvent.

The methanol formed during the reaction can be removed by azeotropic distillation or by scavenging with molecular sieves.

According to these methods the dicarboalkoxy dioxolane derivatives of the present invention are obtained as stable viscous oils. Drying of the crude products in high vacuum and at elevated temperatures removes unreacted starting materials and the compounds of formula I are obtained in high purity (>90%). They can be used as such or can be further purified by flash chromatography.

The citral release preparation of the present invention may be used individually in an amount effective to impart a perceivable quantity of citral in the final product. More commonly, however, the compounds of formula I are mixed with flavor compounds in an amount sufficient to impart the desired flavor to the food product. The amount required to produce the desired overall effect varies depending upon the particular form of the release preparation, the food product in which it will be used and the particular effect desired.

The following examples illustrate the invention without limiting it.

EXAMPLE 1

(E/Z)-(4R,5R)-2-(2,6-Dimethyl-hepta-1,5-dienyl)-[1,3]dioxolane-4,5-dicarboxylic acid diisopropylester (1)

A solution of 20.0 g (85.5 mmol) (R,R)-diisopropyl tartrate, 33.85 g (170.9 mmol) citral dimethyl acetal and 0.5 g pyridinium p-toluene sulfonate in 350 ml MTBE is heated at reflux temperature (55° C.) for 5 h. The clear yellow; reaction mixture is allowed to cool to room temperature and 150 ml saturated $NaHCO_3$ solution is added. The aqueous layer is separated and washed twice with 150 ml MTBE. The combined organic layers are washed with 100 ml brine, dried ($MgSO_4$) and concentrated in vacuo (rotary evaporator). Using a Büchi-Kugelrohrofen the oily residue (47.1 g) is dried in high vacuum (0.1 torr) at 110° C. to give 25.5 g (81%) citral diisopropyl tartrate 1. $^1$H-NMR: 1.30 (d, $CH_3$), 1.31 (d, $CH_3$), 1.61 (s, $CH_3$), 1.68 (s, $CH_3$), 1.79 (d, $CH_3$), 2.0–2.2 (m, 4H, $CH_2$), 4.61 (m, 1H), 4.67 (m, 1H), 5.0–5.2 (m, 3H), 5.36 (m, 1H), 5.91 (dd, 1H); MS: 368 (3, $M^+$), 281 (5), 245 (8), 69 (100), 41 (83).

EXAMPLE 2

(E/Z)-(4R,5R)-2-(2,6-Dimethyl-hepta-1,5-dienyl)-[1,3]dioxolane-4,5-dicarboxylic acid dibutylester (2)

According to the procedure described for the diisopropyl tartrate in Example 1, the citral dibutyl tartrate 2 is obtained in 78% yield. $^1$H-NMR: 0.95 (m, 2 $CH_3$), 1.41 (m, 4H, $CH_2$), 1.55–1.75 (m, 4H, $CH_2$), 1.60 (s, $CH_3$), 1.68 (s, $CH_3$), 1.80 (s, $CH_3$), 2.0–2.2 (m, 4H, $CH_2$), 4.22 (m, 4H, $OCH_2$), 4.68 (m, 1H), 4.76 (m, 1H), 5.1 (m, 1H), 5.46 (m, 1H), 5.91 (dd, 1H); MS: 396 (3, $M^+$), 339 (7), 273 (11), 83 (32), 69 (93), 57 (38), 41 (100).

EXAMPLE 3

(E/Z)-(4R,5R)-2-(2,6-Dimethyl-hepta-1,5-dienyl)-[1,3]dioxolane-4,5-dicarboxylic acid diethylester (3)

According to the procedure described for the citral diisopropyl tartrate in Example 1, the citral diethyl tartrate 3 is obtained in 80% yield.

$^1$H-NMR: 1.32 (m, 2 $CH_3$), 1.61 (s, $CH_3$), 1.67 (s, $CH_3$), 1.80 (d, $CH_3$), 2.0–2.2 (m, 4H, $CH_2$), 4.28 (m, 4H, $OCH_2$), 4.68 (m, 1H), 4.76 (m, 1H), 5.1 (m, 1H), 5.36 (m, 1H), 5.91 (dd, 1H); MS: 340 (3, $M^+$), 267 (5), 217 (22), 69 (100), 41 (80).

EXAMPLE 4

(E/Z)-(4R,5R)-2-(2,6-Dimethyl-hepta-1,5-dienyl)-[1,3]dioxolane-4,5-dicarboxylic acid dimethylester (4)

According to the procedure described for the citral diisopropyl tartrate in Example 1, the citral dimethyl tartrate 4 is obtained in 56% yield.

$^1$H-NMR: 1.61 (s, $CH_3$), 1.70 (s, $CH_3$), 1.80 (t, $CH_3$), 2.0–2.2 (m, 4H, $CH_2$), 3.85 (t, $CH_3$), 4.72 (m, 1H), 4.81 (m, 1H) 5.1 (m, 1H), 5.30 (m, 1H), 5.90 (dd, 1H); MS: 312 (2, $M^+$), 189 (17), 69 (100), 41 (97).

EXAMPLE 5

(E/Z)-(4R,5R)-2-(2,6-Dimethyl-hepta-1,5-dienyl)-[1,3]dioxolane-4,5-dicarboxylic acid dipropylester (5)

According to the procedure described for the citral diisopropyl tartrate in Example 1, the citral dipropyl tartrate 5 is obtained in 74% yield.

$^1$H-NMR: 0.96 (t, $CH_3$), 1.60 (s, $CH_3$), 1.70 (s, $CH_3$), 1.80 (d, $CH_3$), 1.60–1.80 (m, 4H, $CH_2$), 2.0–2.2 (m, 4H, $CH_2$), 4.20 (t, 4H, $OCH_2$), 4.70 (m, 1H), 4.77 (m, 1H), 5.10 (m, 1H), 5.37 (m, 1H), 5.90 (dd, 1H); MS: 368 (1, $M^+$), 281 (3), 245 (13), 69 (100), 41 (82).

EXAMPLE 6

Stability of Compound 1

The stability of compound 1 of Example 1 was tested in a still lemon beverage prepared by 1+5 dilution of lemon/lime-lemon beverage concentrate (210 g) with water (835 g). Formula of the lemon/lime-lemon beverage concentrate used:

TABLE 1

| Ingredient | Parts |
| --- | --- |
| sugar syrup 65 Bx | 1033 g |
| sodium benzoate | 1 g |
| sodium citrate | 2 g |
| citric acid 50% w/w in water | 50 g |
| water | 193 g |

Three 100 ml solutions containing each 100 ppm of the compound 1 were prepared and the decomposition of 1 was determined over a period of 5 days by extraction of 5 ml test solutions samples with hexane, spiked with 100 ppm of ethyl myristate. The extracts were analyzed by GC (Hewlett Packard 6890; column: DB-5, 30 m, 0.32 mm i.d.) and for each data point a mean value based on three measurements was calculated. Assuming a decay following a first order kinetic, $c(t)=c(t_O)\cdot e^{-k}(t-t_O)$, a half life of $t_{1/2}=4$ days was calculated for compound 1.

EXAMPLE 7

Stability of Compound 5

The stability of compound 5 of Example 5 was determined as described for compound 1 in Example 6 and a half life of 11 days was calculated.

EXAMPLE 8

Stability of Compound 3

The stability of compound 3 of Example 3 was determined as described for compound 1 in Example 6 and a half life of 21 h was calculated.

EXAMPLE 9

Preparation of a Citral Release Preparation A), Containing Compound 3

The emulsion according to table 2 was spray dried according to WO-A1 9716078 yielding a powder containing citral diethyl tartrate 3 at a 1% level.

TABLE 2

| Ingredient | parts | Solids weight | dry |
| --- | --- | --- | --- |
| compound (3), 5% in vegetable oil | 90.90 | 20 | |
| Kelcoloids | 1.60 | 0.35 | |

TABLE 2-continued

| Ingredient | parts | Solids weight | dry |
|---|---|---|---|
| Capsul | 68.20 | 15 | |
| maltodextrin | 293.8 | 64.65 | |
| Water | 545.50 | 00 | |

EXAMPLE 10

The ingredients listed in the Table 3 were mixed in 2 quarts of water and were stored in the refrigerator until the time of testing. The samples were tested 24 h and 72 h after the preparation by a group of food technologist specialized in beverages.

TABLE 3

| Ingredient | Control | Sample 1 |
|---|---|---|
| sugar | 175.0 g | 175.0 g |
| citric acid | 4.0 g | 4.0 g |
| Art. Lemon flavor #183555[1)] | 1.06 g | 1.06 g |
| release preparation A) | 0 g | 0.53 g |

[1)]The flavor used is a commercial lemon flavor of Givaudan Roure Flavors Ltd.

The panelists judged sample 1 to be slightly preferred over the control lemon beverage after 24 h and to be greatly preferred after 48 h and 72 h.

EXAMPLE 11

The ingredients listed in the Table 4 were mixed in 2 quarts of water and were stored in the refrigerator until the time of testing. The samples were evaluated by a panelist trained to assess the various attributes of lemon.

TABLE 4

| Ingredient | Control | Sample 1 | Sample 2 |
|---|---|---|---|
| sugar | 175.0 g | 175.0 g | 175.0 g |
| citric acid | 4.0 g | 4.0 g | 4.0 g |
| Art. Lemon flavor #183555[1)] | 1.06 g | 1.06 g | 1.06 g |
| release preparation A) | 0 g | 0.53 g | 1.06 g |

[1)]The flavor used is a commercial lemon flavor of Givaudan Roure Flavors Ltd.

The panelist found that the use of release preparation A) enhanced certain desirable attributes of lemon, especially when used at the level of sample 1. Sample 1, after 24 h: showed enhanced sweetness over control. Sample 1, after 72 h: displayed stronger candy, lemon peely notes (which are two important positive attributes of lemon flavor). Sample 2, after 24 h: showed enhanced sweetness over control. Sample 2, after 72 h: showed a stronger citronellal note (characteristic of lemon) in comparison to control. At the level of sample 2, some increase in negative attributes such as bitter and astringent tastes were observed.

What is claimed is:

1. A citral release preparation comprising at least one dicarboalkoxy dioxolane of formula I:

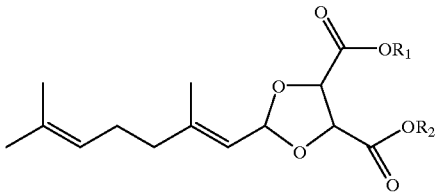

wherein $R_1$ and $R_2$ are the same or different and stand for H, straight or branched alkyl, alkenyl, cycloalkyl, aryl or aralkyl.

2. Citral release preparation containing a dicarboalkoxy dioxolane according to claim 1 and a solid carrier.

3. Citral release preparation containing a mixture of dicarboalkoxy dioxolanes according to claim 1.

4. Citral release preparation according to claim 2 containing an encapsulating agent.

5. Citral release preparation according to claim 2 containing a flavor compound.

6. Citral release preparation according to claim 2 wherein the solid carrier material is maltodextrin.

7. Citral release preparation according to claim 2 wherein the solid carrier material is modified starch.

8. Citral release preparation according to claim 2 wherein the solid carrier material is gum arabicum.

9. Method for preparing a flavor release preparation according to claim 1 by granulating the dicarboalkoxy dioxolane of formula I whereby a fluidized core material is sprayed with an emulsion of the dicarboalkoxy dioxolane of formula I.

10. A method of prolonging the citral characteristics of a citrus-type beverage comprising admixing with the citrus beverage a citral release preparation comprising a carboalkoxy dioxolane of formula I:

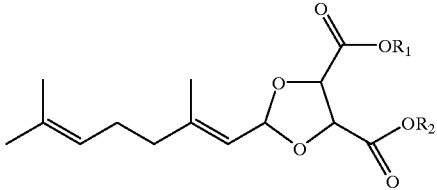

wherein $R_1$ and $R_2$ are the same or different and stand for H, straight or branched alkyl, alkenyl, cycloalkyl, aryl, or aralkyl.

* * * * *

UNITED STATES PATENT AND TRADEMARK OFFICE
CERTIFICATE OF CORRECTION

PATENT NO. : 6,387,431 B1
DATED : May 14, 2002
INVENTOR(S) : Markus Gautschi

It is certified that error appears in the above-identified patent and that said Letters Patent is hereby corrected as shown below:

<u>Title page,</u>
Item [56], References Cited, U.S. PATENT DOCUMENTS, please add the following:
-- 4,296,137    10/1981    Boden
4,280,011    07/1981    DeSimone
3,625,709    12/1971    Mitchell, et al. --

Item [56], References Cited, FOREIGN PATENT DOCUMENTS, please add the following:
-- FOREIGN PATENT DOCUMENTS
97/16078    05/1997    WO
501,645     02/1992    EP --

Item [56], References Cited, OTHER PUBLICATIONS, please add the following:
-- Engel, K., et al., <u>J. Agric. Food Chem.</u>, 39:2249-2252 (1991)
Bedoukian, P.Z., et al., <u>Perfumery and Flavoring Synthetics</u>, 17-18 (1986)
Friedrich, H., et al., <u>Lebensm-Wiss. U Technol.</u>, 11:215-218 (1978)
Friedrich, H., et al., <u>Lebensm-Wiss. U Technol.</u>, 11:316-318 (1978)
Kimura, K., et al., <u>J. Agric. Food Chem.</u>, 31:801-804 (1983)
Schieberle, P., et al., <u>Z. Lebensm Unters Forsch.</u>, 189:26-31 (1989)
Freeburg, E.J., et al., <u>Perfumer & Flavorist</u>, 19:23-32 (1994) --

UNITED STATES PATENT AND TRADEMARK OFFICE
CERTIFICATE OF CORRECTION

PATENT NO. : 6,387,431 B1
DATED : May 14, 2002
INVENTOR(S) : Markus Gautschi

It is certified that error appears in the above-identified patent and that said Letters Patent is hereby corrected as shown below:

<u>Column 8,</u>
Line 35, please correct to read -- ... according to claim 2 by granulating the dicarboalkoxy ... --
Lines 41-42, please correct to read -- ... beverage a citral release preparation comprising a dicarboalkoxy dioxolane of formula I: ... --

Signed and Sealed this

Twenty-fourth Day of September, 2002

Attest:

Attesting Officer

JAMES E. ROGAN
*Director of the United States Patent and Trademark Office*